(12) United States Patent
Brown

(10) Patent No.: US 11,413,186 B2
(45) Date of Patent: Aug. 16, 2022

(54) TRAUMA HEATER SYSTEM

(71) Applicant: Glenn Norman Brown, Williamsburg, VA (US)

(72) Inventor: Glenn Norman Brown, Williamsburg, VA (US)

(*) Notice: Subject to any disclaimer, the term of this patent is extended or adjusted under 35 U.S.C. 154(b) by 1099 days.

(21) Appl. No.: 15/979,389

(22) Filed: May 14, 2018

(65) Prior Publication Data

US 2019/0133818 A1    May 9, 2019

Related U.S. Application Data

(60) Provisional application No. 62/505,564, filed on May 12, 2017.

(51) Int. Cl.
*A61F 7/08* (2006.01)
*A61F 7/03* (2006.01)
*A61F 7/00* (2006.01)

(52) U.S. Cl.
CPC .................. *A61F 7/08* (2013.01); *A61F 7/03* (2013.01); *A61F 2007/006* (2013.01); *A61F 2007/0031* (2013.01); *A61F 2007/0041* (2013.01); *A61F 2007/0088* (2013.01)

(58) Field of Classification Search
CPC ...... A61F 7/03; A61F 7/032; A61F 2007/006; A41D 13/002; A41D 13/0025; A41D 13/005; A41D 13/0051; A41D 13/0053
See application file for complete search history.

(56) References Cited

U.S. PATENT DOCUMENTS

| | | | | |
|---|---|---|---|---|
| 4,068,651 A | * | 1/1978 | Rappaport | A61F 7/032 126/208 |
| 4,174,702 A | * | 11/1979 | Rappaport | A61F 7/032 126/208 |
| 4,691,688 A | * | 9/1987 | Urso | F24C 1/16 126/204 |
| 5,467,760 A | * | 11/1995 | Cox | A61F 7/032 126/204 |
| 8,336,536 B1 | * | 12/2012 | Wood-Putnam | B63C 11/28 126/204 |

* cited by examiner

*Primary Examiner* — Kaitlyn E Smith
(74) *Attorney, Agent, or Firm* — Deidre McAuley

(57) ABSTRACT

A trauma heater system uses the exothermic properties of the reaction between the gas (Co2) and chemical crystals (Group IA and IIA hydroxides and metal hydroxides) to provide heat. Heat generated by the trauma heater system reverses temperature loss in a person's body subjected to lower outside temperature, as in hypothermia, thereby restoring lost body heat and/or maintaining a person's body temperature to prevent hypothermia.

8 Claims, 2 Drawing Sheets

US 11,413,186 B2

TRAUMA HEATER SYSTEM

I. CROSS-REFERENCE APPLICATION

The present application is a non-provisional application claiming priority to Provisional Application No. 62/505,564 filed May 12, 2017, the contents of which are incorporated herein in its entirety.

II. FIELD OF THE INVENTION

The present invention relates to a trauma heater system. In particularly, the present invention relates to heater that uses exothermic properties of the reaction between the gas (Co2) and chemical crystals (Group IA and IIA hydroxides and metal hydroxides) to provide heat.

III. BACKGROUND OF THE INVENTION

There are several heating systems which are used to generate heat in different types of environments (indoors and outdoors). One type of heating system is a flammable gas stove which may be used in a mountaineering environment, for example. A mountaineer that may be melting ice and snow, for drinking water, within a tent may use the flammable gas stove in which a pot filled with ice and snow is placed on upon the flammable gas stove. There are several concerns when using a flammable gas stove that may include the gas emissions from the flame containing carbon monoxide and requiring the mountaineer to ventilate the tent in order to prevent carbon monoxide poisoning. Further, flammable gas stoves are highly inefficient at extremely high altitudes. Due to less dense air at high altitudes, the flames produced from the stove are less hot. At high altitude, there are less oxygen molecules per square foot than at lower elevations. Flammable gas stoves also present a hazard to the mountaineer and their equipment when incorrectly used. It is not uncommon for an uncontrolled fire to occur from the improper use of the flammable gas stove.

Another type of heating system is a fixed mounted hot-water radiator within a room of a domicile. The use of a fixed mounted hot-water radiator requires the use of a furnace to heat hot water. The hot water travels through pipes from the furnace to the hot-water radiator in a room. As the hot water travels through the pipes, the heat of the water dissipates before reaching the hot-water radiator in the room. Therefore, the travel distance between the furnace and the room's hot-water radiator creates inefficiency with heating the room.

There are some heating systems which achieve heat, via an exothermic reaction, through the combining of chemicals. For example, United States Patent Application Serial Number 2012/0210996 A1 which relates to a flameless heating apparatus for food products that achieves exothermic heat, by adding water to an alloy powder dispersed throughout a porous polyethylene matrix, to create a non-sustained heating effect without directing that heat towards the object being heated. However, the gas emission from the chemical mixture, hydrogen, is not conducive human's inhalation of the hydrogen rich air within a confined environment.

Other heating systems have been created that combine Group IA and IIA metal hydroxides and carbon dioxide. For example, U.S. Pat. No. 5,964,221 which relates to a re-breather adsorbent system for use in a self-contained breathing apparatus. This breathing device uses mixtures of Group IA and IIA metal hydroxides for "scrubbing" the carbon dioxide from a person's exhaled breath. "Scrubbing" is the process of converting carbon dioxide to oxygen, thus enabling a person to retain and reuse some, or all, of their expired breath while using a breathing apparatus. The heat derived from the exothermic reaction of the "scrubbing" process is treated as a waste by-product and left simply to disperse into the surrounding environment.

IV. SUMMARY OF THE INVENTION

The embodiments of the present invention obviate the above-identified problems by providing a trauma heater uses the exothermic properties of the reaction between the gas (Co2) and chemical crystals (Group IA and IIA hydroxides and metal hydroxides) to provide heat. Any heat generated by the trauma heater reverses temperature loss in a person's body subjected to lower outside temperature, as in hypothermia, thereby restoring lost body heat and/or maintaining a person's body temperature to prevent hypothermia.

According to embodiments of the present invention, the trauma heater when used will provide heat to a small enclosed area. When placed between the armpit and chest will heat the body core, or in between the thighs (groin area) will heat the femoral arteries of the legs through direct contact.

The foregoing has broadly outlined some of the aspects and features of the embodiment, which should be construed to be merely illustrative of various potential applications of the disclosure. Other beneficial results can be obtained by applying the disclosed information in a different manner or by combining various aspects of the disclosed embodiments. Accordingly, other aspects and a more comprehensive understanding may be obtained by referring to the detailed description of the exemplary embodiments taken in conjunction with the accompanying drawings, in addition to the scope defined by the claims.

V. BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

Figure 1:
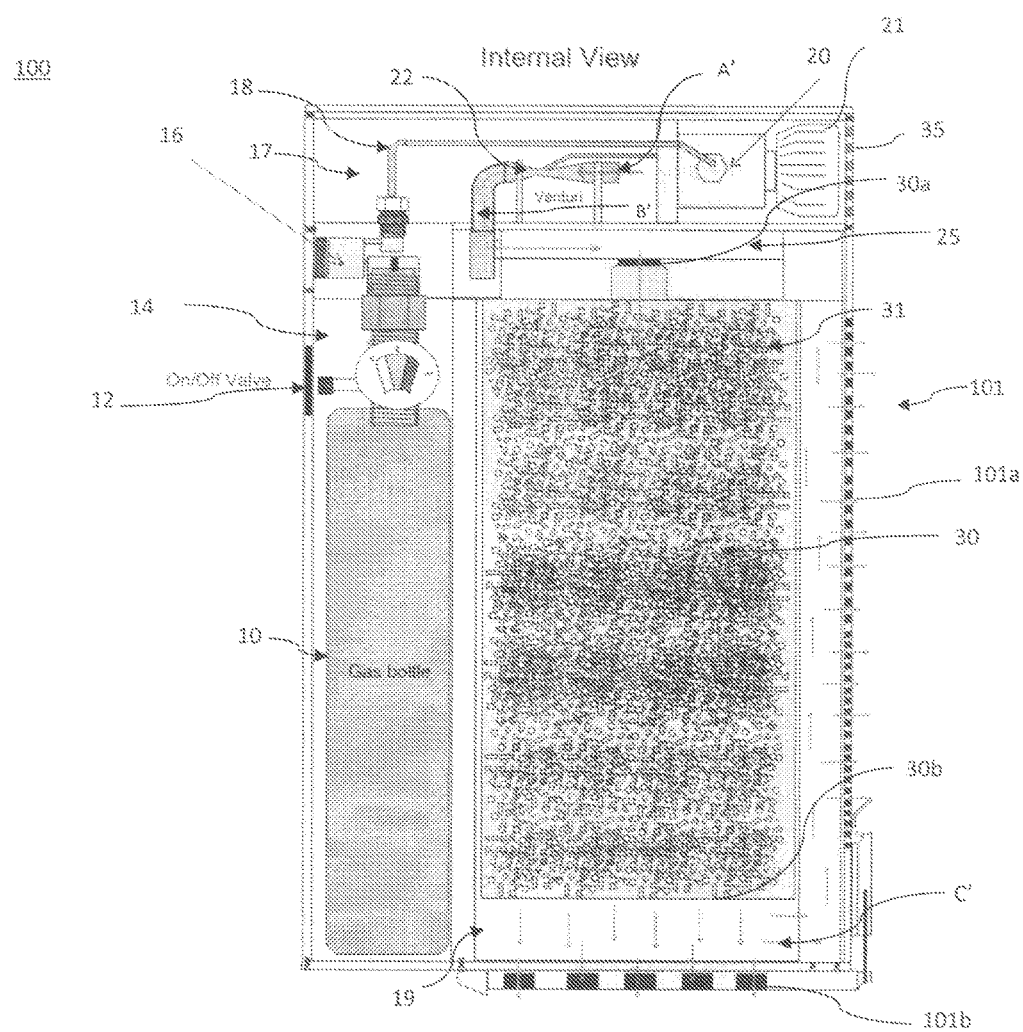
FIG. 1 is a schematic view illustrating the trauma heater system that can be implemented within one or more embodiments of the present invention.

The drawings are only for purposes of illustrating preferred embodiments and are not to be construed as limiting the disclosure. Given the following enabling description of the drawings, the novel aspects of the present disclosure should become evident to a person of ordinary skill in the art. This detailed description uses numerical and letter designations to refer to features in the drawings. Like or similar designations in the drawings and description have been used to refer to like or similar parts of embodiments of the invention. VI.

DETAILED DESCRIPTION OF THE INVENTION

As required, detailed embodiments are disclosed herein. It must be understood that the disclosed embodiments are merely exemplary of various and alternative forms. As used herein, the word "exemplary" is used expansively to refer to embodiments that serve as illustrations, specimens, models, or patterns. The figures are not necessarily to scale and some features may be exaggerated or minimized to show details of particular components.

In other instances, well-known components, apparatuses, materials, or methods that are known to those having ordinary skill in the art have not been described in detail in order to avoid obscuring the present disclosure. Therefore, specific structural and functional details disclosed herein are not to be interpreted as limiting, but merely as a basis for the claims and as a representative basis for teaching one skilled in the art.

Embodiments of the present invention will now be discussed below with reference to FIGS. 1 and 2. The present invention is not limited to use of any particular components or combination of components and may vary as necessary.

As discussed above, embodiments of the present invention provide a trauma heater system that uses the exothermic properties of the reaction between the gas ($Co_2$) and chemical crystals (Group IA and IIA hydroxides and metal hydroxides), to provide heat. An example, is "Sofnolime®" (or Soda Lime).

According to embodiments, the heat generated by heater system will reverse temperature loss in a person's body subjected to lower outside temperature, as in hypothermia, by restoring lost body heat or maintains a person's body temp to prevent hypothermia.

The heater system when used will provide heat to a small enclosed area. Specifically, the heater system is a personal, portable heater for use for an individual person. The heater system can be worn by the individual person. When placed between the armpit and chest of a person, the heater system will heat the body core, or in between the thighs (groin area) will heat the femoral arteries of the legs through direct contact. Additional details of the heater system will be discussed below with reference to FIGS. 1 and 2.

As shown in FIG. 1, a heater system 100 is provided. Within the heater system 100 includes a body 101 having openings 101a and 101b at a side and bottom surface thereof, gas is introduced into the heater system 100 via a gas bottle 10. The body 101 includes a first chamber 14, a second chamber 17 and a third chamber 19 along with a first expansion chamber 16 and a second expansion chamber 25, as shown. The gas bottle 10 is a removable bottle that is used to store the gas and is designed to be removed when the gas is depleted. The gas bottle 10 can be of any size or type, e.g., a 3.2 ounce disposable single-use bottom or reuseable bottle (e.g., 3 ounce, 6 ounce, 9 ounce, 12 ounce bottle). The gas leaves the bottle 10 through an on/off valve 12 (e.g., a Schrader valve) into the first chamber 14. The first chamber 14 is threaded to accept (i.e., receive) the gas bottle 10. Gas flow enters the first expansion chamber 16 allowing the gas to expand. Flow from the first expansion chamber 16 enters the small threaded orifice whereas the gas enters the piping 18 (as shown in the top portion of FIG. 1) to the regulator 20.

According to an embodiment of the present invention, the regulator 20 having a handle 21 reduces the high pressure gas to a lower manageable pressure. The regulator 20 also acts to regulate the reaction by controlling the gas pressure/flow thus controlling the temperature of the heater system 100.

Gas flow leaves the regulator 20 entering through an orifice into the venturi 22. For example, the regulator 20 may regulate gas from an input pressure of up to 3600 psig, the output pressure into the venturi 22 would be approximately 0-10 psig. The venturi 22 creates a high velocity of the applied gas thus creating a vacuum, this vacuum pulls in outside air (depicted as A' arrow) from holes 35, increasing the volume of gas into the heater system 100. The combined gases (depicted as B' arrow) move into the second expansion chamber 25 to expand and mix one last time, the gas now enters the canister 30. The canister 30 includes an opening 30a at a top surface and an opening 30b at a bottom surface thereof to receive the combined gases and to exit heat therefrom respectively, and contains chemical granules 31, where the reaction takes place. According to one embodiment, the chemical granules 31 are crystals (Group IA and IIA hydroxides and metal hydroxides). The present invention is not limited to any particular amount of chemical granules and can be varied as necessary.

During this reaction, the gases move through the canister 30 where the $CO_2$ is absorbed into the chemical granules 31 and causing the reaction, this reaction is exothermic and gives off heat. The heat and the outside air will continue through the canister 30 and exit through the bottom and sides 101a and 101b of the body 101 of the heater system 100, as indicated by C' arrows.

Figure 2:
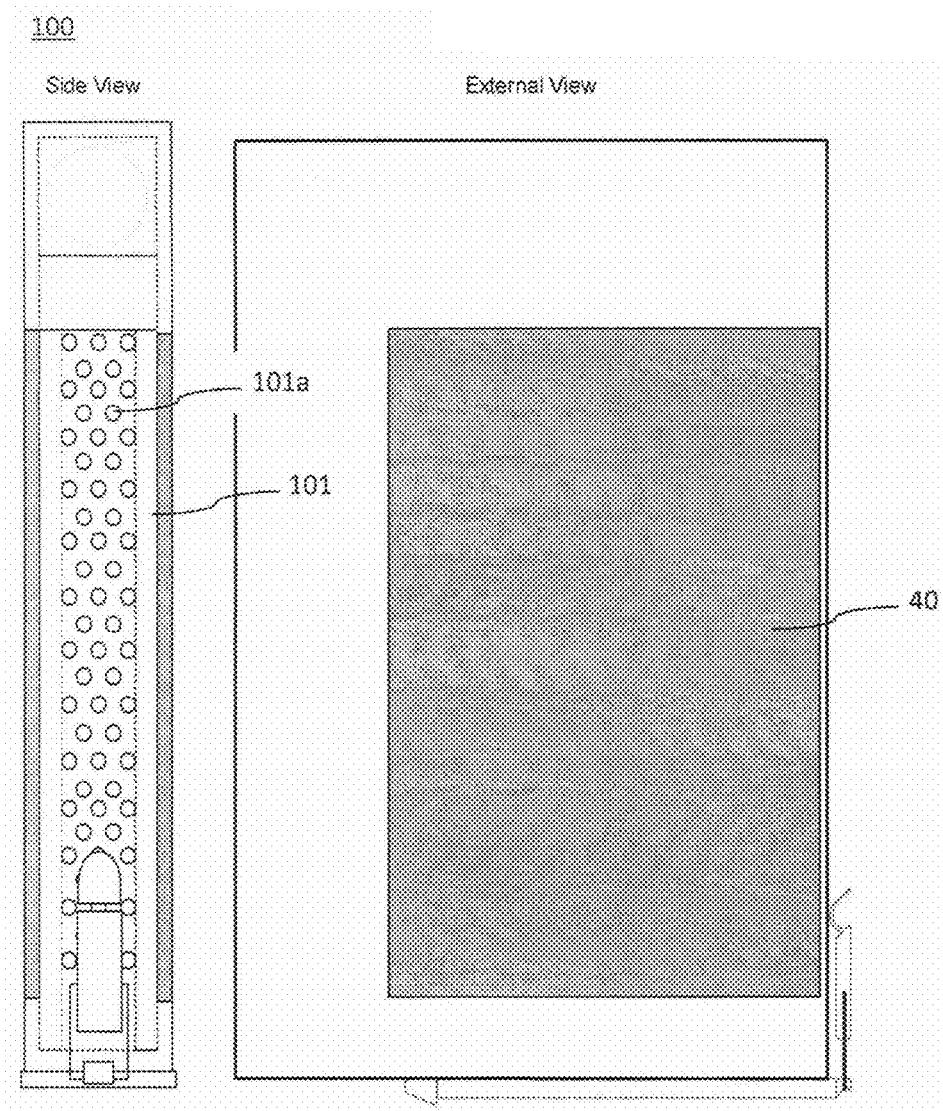
FIG. 2 is a schematic view illustrating an external view of the trauma heater system that can be implemented within one or more embodiments of the present invention.

Further, as shown in the external view of the heater system 100 in FIG. 2, the sides 101a of the body 101 of the heater system 100 will also radiate heat. The conductive area 40 (e.g., conductive plate of metal or ceramic or other thermally conductive material) will conduct the most heat through the body 101 of the heater system 100. Once the chemical granules 31 are saturated through the reaction, the canister 30 shown in FIG. 1 can be removed and replaced, the old canister can be discarded according to the IAW the Federal and state guidelines.

The heat radiating from the heater system 100 is of a temperature range which is ambient (which is the temperature when the canister 30 is inserted before use) up to an exceeding for example, approximately 200 degrees Fahrenheit (F). According to an embodiment of the present invention, the temperature may only be limited to the amount of chemical granules 31 and gas volume used. According to one embodiment, the temperature may range from between approximately 100 degrees F. through approximately 180 degrees F. and can vary to suit the environment to which applied.

According to additional embodiments of the present invention, the use of the regulator 20 and venture 22, the heater system 100 will move air as if it had a fan inside pushing the air. The heater system 100 provides several advantages such as not requiring batteries or any electrical device to operate.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A heater system to be worn by an individual person, comprising:
    a body comprising:
        a first chamber, a second chamber and a third chamber for housing components of the heating system;
        first openings in a side surface and second openings in a bottom surface of the body,
        a gas bottle configured to store gas therein,
        the first chamber configured to receive the gas bottle therein,
    a first expansion chamber configured to receive the gas from the gas bottle of the first chamber and enable the gas to expand therein,
    a regulator disposed within the second chamber and being connected with the first expansion chamber via a piping portion in the second chamber, wherein the gas enters the piping portion and is transmitted to the regulator, the regulator being configured to regulate a reaction by controlling the gas pressure and flow thereof,
    a venturi in the second chamber adjacent to the regulator, wherein the gas flows from the regulator through an orifice into the venturi, and the venturi is configured to create a high velocity of the gas to create a vacuum, the vacuum pulling outside air from holes in a side surface of the second chamber into the heater system to increase a volume of the gas into the heater system, forming combined gases,
    a second expansion chamber configured to receive the combined gases and to expand and mix the combined gases, and
    a canister received within the third chamber and comprising chemical granules wherein the combined gases flow into the canister, and carbon dioxide ($CO_2$) is absorbed into the chemical granules causing an exothermic reaction to generate heat, wherein the heat and outside air flow through the canister and exits from the first openings in the side surface and the second openings in the bottom surface of the body.

2. The heater system of claim 1, wherein the chemical granules are formed of Group IA and IIA hydroxides and metal hydroxides.

3. The heater system of claim 1, wherein the gas bottle is replaceable.

4. The heater system of claim 1, wherein the canister is replaceable.

5. The heater system of claim 1, wherein external sides of the heater system radiate the heat.

6. The heater system of claim 5, further comprising:
    a conductive area configured to conduct heat through the external sides of the heater system.

7. The heater system of claim 6, wherein the conductive area comprises a conductive plate formed of a thermally conductive material.

8. The heater system of claim 1, wherein the heater system is operated without internal or external power supply.

* * * * *